United States Patent [19]  [11] 4,428,956
Cragoe, Jr. et al.  [45] Jan. 31, 1984

[54] 4-HYDROXY-5-SUBSTITUTED-3-(2H)-ISO-THIAZOLONE-1,1-DIOXIDE DERIVATIVES USEFUL IN TREATING URINARY TRACT CALCIUM OXALATE LITHIASIS

[75] Inventors: Edward J. Cragoe, Jr., Lansdale; Clarence S. Rooney, Worcester, both of Pa.; Haydn W. R. Williams, Dollard des Ormeaux, Canada

[73] Assignees: Merck & Co., Inc.; Merck Sharp & Dohme (I.A.) Corp., both of Rahway, N.J.

[21] Appl. No.: 221,173

[22] Filed: Dec. 29, 1980

[51] Int. Cl.³ .................. C07D 275/02; A61K 31/44
[52] U.S. Cl. .................................. 424/270; 548/206; 548/213
[58] Field of Search ................ 548/206, 213; 424/270

[56] References Cited
U.S. PATENT DOCUMENTS 3,849,430 11/1974 Lewis ................................. 424/270
4,067,878 1/1978 Miller ................................. 424/270
4,346,094 8/1982 Beck et al. ......................... 548/206

OTHER PUBLICATIONS

Lewis et al., J. Het. Chem., 8, p. 591 (1971).
Burger, Medicinal Chemistry, p. 42.
Randall et al., J. Med. Chem., 22, p. 608.

Primary Examiner—Donald G. Daus
Assistant Examiner—G. Hendricks
Attorney, Agent, or Firm—Theresa Y. Cheng; Raymond M. Speer

[57] ABSTRACT

4-Hydroxy-5-substituted-3(2H)-isothiazolone-1,1-dioxide derivatives of the formula:

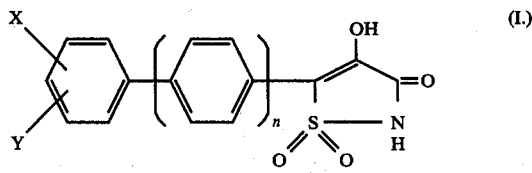

where
X and Y are independently selected from the group consisting of hydrogen, halogen, and $C_{1-6}$ alkyl; provided that positions 2 and 6 of the substituted phenyl moiety may not be substituted; and n is 0 or 1;
or a pharmaceutically acceptable salt thereof; useful in treating urinary tract, especially renal calcium oxalate lithiasis.

13 Claims, No Drawings

4-HYDROXY-5-SUBSTITUTED-3-(2H)-ISO- THIAZOLONE-1,1-DIOXIDE DERIVATIVES USEFUL IN TREATING URINARY TRACT CALCIUM OXALATE LITHIASIS

BACKGROUND OF THE INVENTION

1. Field of the Invention

The present invention is concerned with novel 4-hydroxy-5-substituted-3(2H)-isothiazolone-1, 1-dioxide compounds useful in treating urinary tract, especially renal calcium oxalate lithiasis. The novel compounds of the present invention act as potent inhibitors of the enzyme glycolate oxidase.

The present invention is also concerned with a method of treating or preventing the formation of calcium oxalate urinary tract lithiasis, especially kidney or bladder stones, as well as pharmaceutical compositions useful in such a method, containing the novel 4-hydroxy-5-substituted-3(2H)-isothiazolone-1, 1-dioxide compounds as active ingredient.

Close to 70% of kidney stones are composed partially or predominantly of calcium oxalate; yet there is no satisfactory drug specific for the treatment of calcium oxalate urinary tract lithiasis, nor for prophylactic use by people prone to recurrent attacks of this disease.

Calcium oxalate lithiasis, the formation of stony concretions composed partially or predominantly of calcium oxalate, may occur at different points in the urinary tract, and is especially a problem in the kidney and in the bladder.

Approximately 70% of all renal calculi contain oxalate as the main anionic component of the matrix. In many, but not all patients, the condition is associated with a higher than normal level of metabolically produced oxalate.

Common procedures for treatment of renal lithiasis due to calcium oxalate consist of surgical removal of stones, or control of the diet to restrict intake of calcium and/or oxalate combined with ingestion of large quantities of water to dilute the urine. Attempts at chemotherapy have included the administration of magnesium oxide, orthophosphate, cellulose phosphate, isocarboxazide, thiazide diuretics, allopurinol and succinimide. Limited success has been realized so far by these drug approaches. No drug which specifically inhibits the biosynthetic formation of oxalic acid is available for the treatment of calcium oxalate urinary tract, especially renal lithiasis.

The major precursor of oxalate is glyoxylate. Thus, approaches to the reduction of the biosynthetic output of oxalic acid focus on (a.) the prevention of the conversion of glyoxylate to oxalate, and/or (b.) restriction of the production of glyoxylate from its precursors. A major pathway for the biosynthesis of oxalate can be represented as follows:

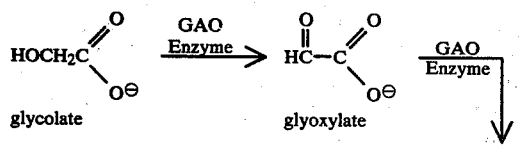
glycolate    glyoxylate

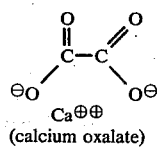
(calcium oxalate)

The same enzyme glycolate oxidase participates both in the biosynthesis of glyoxylate and, in its oxidation to oxalate. An inhibitor of the enzyme will act to block at two key points in the chain of reactions contributing to the production of oxalic acid. As a direct consequence of reducing oxalic acid levels in the urine with the compounds of this invention, the formation of oxalate calculi will be reduced or prevented in individuals whose urinary oxalate is primarily of metabolic origin.

The novel 4-hydroxy-5-substituted-3(2H)-isothiazolone-1,1-dioxide compounds described herein are potent inhibitors of glycolate oxidase and are thus useful in the treatment and prevention of urinary tract lithiasis, especially renal disease due to calcium oxalate stone formation in the kidney. As inhibitors of glycolate oxidase, the novel compounds of the present invention may also be useful in the treatment of primary hyperoxaluria. In the genetically inherited diseases designated hyperoxaluria types I and II, large quantities of oxalic acid are produced metabolically. Crystallization of calcium oxalate, occurring not only in the kidney and bladder, but in other tissues as well, frequently results in early death. The novel compounds of this invention may prove of value in the treatment of these rare but serious disease states.

2. Brief Description of the Prior Art

Glycolic acid oxidase inhibitors are described in U.S. Pat. Nos. 4,178,386; 4,207,329; and 4,233,452; as well as co-pending application Ser. No. 047,412, filed June 11, 1979. 5-Substituted-3(2H)-isothiazolone-1,1-dioxide compounds are described in Lewis et al., *J. Het. Chem.*, 8, p. 591 (1971). However, none of the compounds described in any of the above would suggest the novel 4-hydroxy-5-substituted-3(2H)-isothiazolone-1,1-dioxide compounds of the present invention.

SUMMARY OF THE INVENTION

The novel 4-hydroxy-5-substituted-3(2H)-isothiazolone-1,1-dioxide compounds of the present invention which are useful in treating and preventing urinary tract calcium oxalate lithiasis, especially the formation of calcium oxalate kidney or bladder stones, can be shown by the following formula:

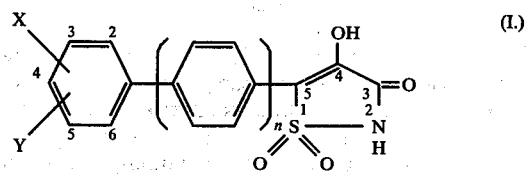

where
X and Y are independently selected from the group consisting of hydrogen, halogen, and $C_{1-6}$ alkyl; provided that positions 2 and 6 of the substituted phenyl moiety may not be substituted; and n is 0 or 1;
or a pharmaceutically acceptable salt thereof.
Particularly preferred compounds of Formula I are the following:

4-hydroxy-5-phenyl-3(2H)-isothiazolone-1,1-dioxide;
5-(3,4-dichlorophenyl)-4-hydroxy-3(2H)-isothiazolone-1,1-dioxide;
5-[4'-chloro-(1,1'-biphenyl)-4-yl]-4-hydroxy-3(2H)-isothiazolone-1,1-dioxide.

Included within the scope of the present invention are the pharmaceutically acceptable salts of the 4-hydroxy-5-substituted-3(2H)-isothiazolone-1,1-dioxide compounds.

Formula I compounds are organic acids with a pKa in the range of 2 to 5 and thus can be used in the form of salts derived from inorganic or organic bases. Included among such salts are the following: metallic cations such as aluminum, calcium, lithium, magnesium, potassium, sodium, and zinc; and organic cations such as choline, diethanolammonium, n-methylglucammonium, ethanolammonium, diethylammonium, and triethanolammonium. Neutralization can be carried out by a variety of procedures known to the art to be generally useful for the preparation of such salts. The choice of the most suitable procedure will depend on a variety of factors including convenience of operation, economic considerations, and particularly the solubility characteristics of the particular free base, the acid, and the acid addition salt. Water or oil-soluble or dispersible products are thereby obtained.

The Formula I compounds can be administered to patients (both human and animal) having, or being prone, to calcium oxalate kidney or bladder stone disease by formulating them in a composition such as tablet, capsule of elixir for oral administration. Sterile solutions or suspensions can be used for parenteral administration. About 25 to 500 mg of a compound of Formula I or a pharmaceutically acceptable salt is compounded with a pharmaceutically acceptable vehicle, carrier, excipient, binder, preservative, stabilizer, flavor, etc., in a unit dosage form as called for by accepted pharmaceutical practice. The amount of active substance in the composition is such that dosage in the range indicated is obtained. The total daily dose administered to patients having or prone to calcium oxalate kidney or bladder stone disease will be in the 50 mg to 2000 mg range with a preferred daily dose being 100 mg to 1000 mg of active ingredient. It will be realized by those skilled in the art that the dosage range for any particular patient (animal or human) will depend upon the severity of the disease treated, weight of the patient and any other condition which the physician or other person skilled in the art will take account of.

Illustrative of the adjuvants which may be incorporated in tablets, capsules and the like are the following: a binder such as gum tragacanth, acacia, corn starch or gelatin; an excipient such as dicalcium phosphate; a distintegrating agent such as corn starch, potato starch, alginic acid and the like; a lubricant such as magnesium stearate; a sweetening agent such as sucrose, lactose, or saccharin; a flavoring agent such as peppermint, oil of wintergreen or cherry. When the dosage unit form is a capsule, it may contain in addition to materials of the above type a liquid carrier such as a fatty oil. Various other materials may be present as coatings or to otherwise enhance the pharmaceutical elegance of the preparation. For instance, tablets may be coated with shellac, sugar or the like. A syrup of elixir may contain the active compound, sucrose as a sweetening agent, methyl and propyl parabens as preservatives, a dye, and a flavoring such as cherry or orange flavor.

Sterile compositions for injection can be formulated according to conventional pharmaceutical practice by dissolving or suspending the active substance in a conventional vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The 4-hydroxy-5-substituted-3(2H)-isothiazolone-1,1-dioxide compounds of Formula I may be prepared in accordance with a reaction scheme which may be illustrated as follows:

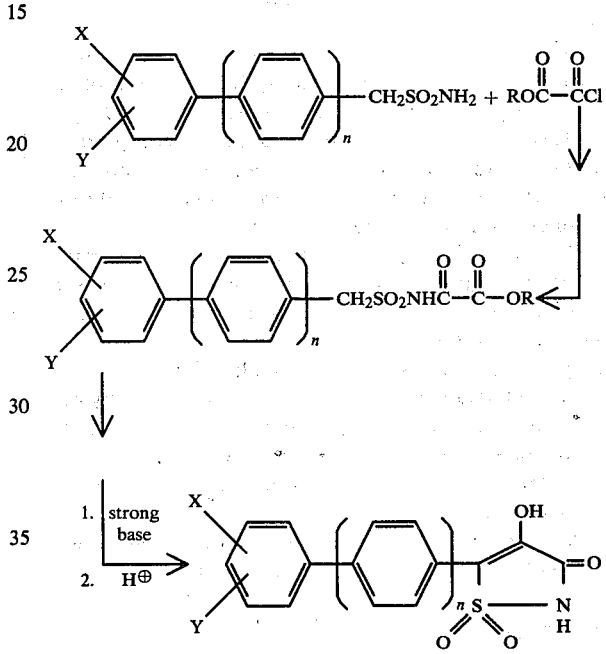

where R is $C_{1-4}$ alkyl, preferably methyl or ethyl; and X, Y and n have the same meaning as above.

The first step of the reaction, in which the substituted benzylsulfonamide or biphenylmethanesulfonamide is reacted with $C_{1-4}$ alkyl oxalyl chloride, can be carried out neat in an excess of $C_{1-4}$ alkyl oxalyl chloride, with heating to about 100° C., followed by removal of the excess $C_{1-4}$ alkyl oxalyl chloride. Alternatively, an alkali metal salt of the benzylsulfonamide or biphenylmethanesulfonamide may be reacted with the $C_{1-4}$ alkyl oxalyl chloride in an aprotic solvent such as tetrahydrofuran or a mixture of tetrahydrofuran and toluene. Since the $C_{1-4}$ alkyl benzylsulfonyloxamates and $C_{1-4}$ alkyl biphenylylmethanesulfonyloxamates which are produced are acidic, use of the alternative procedure requires acidification in order to obtain release of the desired product.

In the second step, reaction of the $C_{1-4}$ alkyl benzylsulfonyloxamate and alkyl biphenylylmethanesulfonyloxamate intermediates in polar solvents such as dimethylformamide, tetrahydrofuran or ethanol, with a strong base such as potassium tert-butoxide, sodium ethoxide or the like, leads to intramolecular acylation and formation of the desired 4-hydroxy-5-substituted-3(2H)-isothiazolone-1,1-dioxide product as its salt. Acidification with mineral acid gives the desired product in its protonated form.

The substituted benzylsulfonamide and biphenylyl-methanesulfonamide starting materials may be prepared in accordance with methods well known in the art. For example, a generally applicable route to these starting materials may be illustrated as follows:

Following are examples which illustrate the preparation of representative compounds and compositions falling with the present invention, although no limitation is thereby intended.

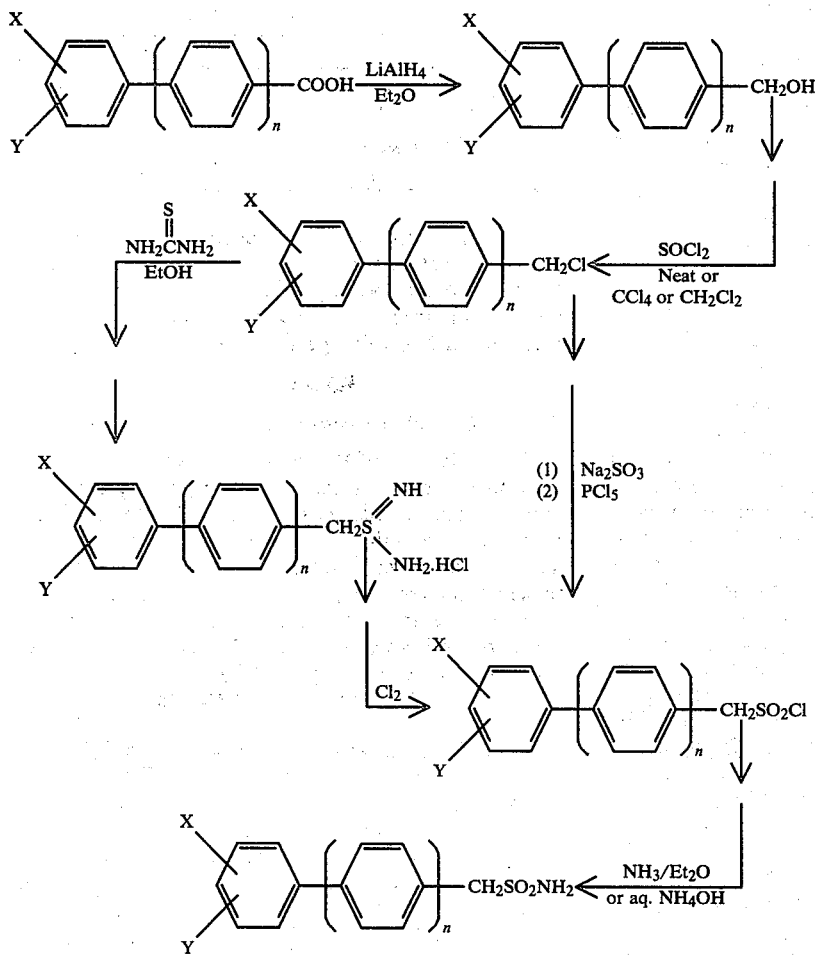

The benzyl halides and biphenylmethyl halide reagents required for the preparation of the corresponding benzyl and biphenylylmethylsulfonamides can also be prepared by other procedures well known in the art. For example, a detailed procedure for conversion of benzoic acids and biphenylylcarboxylic acids to benzyl chloride and biphenylylmethyl chloride derivatives is described by Barclay et al., Can. J. Chem., 50, 2318 (1972). The procedure employing thiourea for conversion of arylmethylchlorides to the corresponding sulfonyl chlorides is well known in the art. See, for example, Chem. Abs. 87, 201092b (1977). An alternative procedure which is also well known for the conversion of arylmethyl chlorides to the corresponding sulfonyl chlorides involves reaction with sodium sulfite to give the arylmethyl sulfonic acid sodium salt, followed by reaction with phosphorus pentachloride. See, for example, Farrar, J. Chem. Soc., 3063 (1960); and Clutterbuck and Cohen, J. Chem. Soc., 123, 2507 (1923). The benzylsulfonyl chlorides and biphenylylmethanesulfonyl chlorides, on reaction with ammonia in an inert solvent such as diethyl ether, or with concentrated aqueous ammonium hydroxide, give rise to the benzylsulfonamide and biphenylylmethylsulfonamide starting materials.

EXAMPLE 1

4-Hydroxy-5-phenyl-3(2H)-isothiazolone-1,1-dioxide

Step A. Methyl N-(benzylsulfonyl)oxamate

A mixture of benzylsulfonamide (6 g., 0.035 mol) and methyl oxalyl chloride (15 ml., 0.16 mol) was heated at 100°–120° C. for one hour. On evaporation there was obtained methyl N-benzylsulfonyloxamate (7.7 g., 0.029 mol) m.p. 117°–122° C. Anal. Calc'd. for $C_{10}H_{11}NO_5S$: % 46.69; % H, 4.31; % N, 5.44. Found: % C, 47.06; % H, 4.32; % N, 5.41.

Step B. 4-Hydroxy-5-phenyl-3(2H)-isothiazolone-1,1-dioxide

To a solution of methyl N-benzylsulfonyloxamate (2.0 g., 0.077 mol) in dimethyl formamide (15 ml.) was added in portions potassium tert-butoxide (1.74 g., 0.016 md). After stirring overnight, the solids were removed by filtration and washed with ether. The filtrate was evaporated to dryness. The solid residue, combined with the first fraction, was dissolved in a small volume of water. The aqueous solution was made strongly acidic by the addition of concentrated hydrochloric acid. After cooling at 0° C. for one hour, there was obtained on filtration the title compound (0.51 g.) m.p. 240°–251° C. (dec.). Anal. Calc'd. for $C_9H_7NO_4S$: % C, 48.00; % H, 3.13; % N, 6.22. Found: % C, 48.00; % H, 3.12; % N, 6.45. When 4-chlorobenzylsulfonamide is employed as the starting material in Example 1 in place of benzylsulfonamide, and the procedures of Steps A and B are followed, there is obtained 5-(4-chlorophenyl)-4-hydroxy-3(2H)-isothiazolone-1,1-dioxide. Similarly, when 4-methylbenzylsulfonamide is employed as the starting material in Example 1, there is obtained 4-hydroxy-5-(4-methylphenyl)-3(2H)-isothiazolone-1,1-dioxide. When 3,4-dichlorobenzylsulfonamide is employed as the starting material in Example 1, there is obtained 5-(3,4-dichlorophenyl)-4-hydroxy-3(2H)-isothiazolone-1,1-dioxide. And when 3,5-diethylbenzylsulfonamide is employed as the starting material in Example 1, there is obtained 5-(3,5-diethylphenyl)-4-hydroxy-3(2H)-isothiazolone-1,1-dioxide.

EXAMPLE 2

5-[1,1'-Biphenyl)-4-yl]-4-hydroxy-3-(2H)-isothiazolone-1,1-dioxide

Step A. [1,1'-Biphenyl)-4-yl]methanesulfonamide

A mixture of [(1,1'-biphenyl)-4-yl]methyl chloride (10.1 g., 0.05 Mol), thiourea (4.0 g., 0.052 Mol) and ethanol (100 ml.) is heated under reflux for 4 hours, and then allowed to stand at room temperature overnight. The ethanol is removed under vacuum and a small volume of acetone is added to the residue. Filtration gives 5-[(1,1'-biphenyl)-4-yl]methylisothiouronium chloride. Into a mixture of the isothiouronium chloride intermediate in glacial acetic acid (100 ml.) is passed chlorine gas for 15 minutes at ice bath temperature. After stirring for another 15 minutes, the mixture is filtered to give crude [(1,1'-biphenyl)-4-yl] methanesulfonyl chloride. The crude product is recrystallized from ether-petroleum ether.

The sulfonyl chloride intermediate is allowed to react with concentrated ammonium hydroxide (150 ml.) at room temperature for 30 minutes. Filtration provides [1,1'-biphenyl)-4-yl]methanesulfonamide.

Step B. Methyl N-[(1,1'biphenyl)-4-yl]methanesulfonyl]oxamate

When the procedures of Step A, Example 1, is followed, employing [(1,1'-biphenyl)-4-yl]methanesulfonamide in place of benzylsulfonamide, there is obtained the title compound.

Step C. 5-[(1,1'Biphenyl)-4-yl]-4-hydroxy-3(2H)-isothiazolone-1,1-dioxide

When the procedure of Step B, Example 1 is followed, employing methyl N-[[(1,1'-biphenyl)-4-yl]methanesulfonyl]oxamate in place of methyl N-benzylsulfonyloxamate, there is obtained 5-[(1,1'-biphenyl)-4-yl]-4-hydroxy-3(2H)-isothiazolone-1,1-dioxide.

When the procedure of Example 2 is followed, except that [4'-chloro-(1,1'-biphenyl)-4-yl]methyl chloride is employed as the starting material in place of [(1,1'-biphenyl)-4-yl]methyl chloride, there is obtained 5-[4'-chloro-(1,1'-biphenyl)-4-yl]-4-hydroxy-3(2H)-isothiazolone-1,1-dioxide. Similarly, when [4'-methyl-(1,1'-biphenyl)-4-yl]methyl chloride is employed as the starting material, there is obtained 5-[4'-methyl-(1,1'-biphenyl)-4-yl]-4-hydroxy-3(2H)-isothiazolone-1,1-dioxide. When [3'-bromo-(1,1'-biphenyl)-4-yl]methyl chloride is employed as the starting material, there is obtained 5-[3'-bromo'(1,1'-biphenyl)-4-yl]-4-hydroxy-3(2H)-isothiazolone-1,1-dioxide. And when [3',4'-dichloro-(1,1'-biphenyl)-4-yl]methyl chloride is employed as the starting material, there is obtained 5-[3',4'-dichloro-(1,1'-biphenyl-4-yl]-4-hydroxy-3(2H)-isothiazolone-1,1-dioxide.

EXAMPLE 3

Dry-filled capsules containing 50 mg. of Active Ingredient per Capsule

| Ingredient | Amount Per Capsule |
|---|---|
| 4-hydroxy-5-phenyl-3(2H)—isothiazolone-1,1-dioxide | 100 mg. |
| Lactose | 149 mg. |
| Magnesium Stearate | 1 mg. |
| Capsule (Size No. 1) | 250 mg. |

The active ingredient is reduced to a No. 60 powder and then lactose and magnesium stearate are passed through a No. 60 bolting cloth onto the powder and the combined ingredients admixed for 10 minutes and then filled into a No. 1 dry gelatin capsule.

EXAMPLE 4

Glycolate Oxidase Enzyme Inhibition

The usefulness of the compounds of the present invention in treating urinary tract, especially renal, calcium oxalate lithiasis, was shown by the ability of those compounds to inhibit the glycolate oxidase enzyme. This inhibition was determined by observing the extent to which the test compound blocked the activity of the enzyme. The activity of the enzyme, in turn, was measured by following the rate of reduction of sodium 2,6-dichlorophenol-indophenol by sodium glycolate in the presence of the enzyme. The enzyme was pig liver glycolate oxidase. The reaction was followed spectrophotometrically at 600 nm. The assay was conducted at 25° C. in a 0.10 M phosphate buffer, pH 7.0, containing 3 mM EDTA. Initial substrate concentrations were $5 \times 10^{-5}$ M of sodium 2,6-dichlorophenol-indophenol and $2 \times 10^{-4}$ M of sodium glycolate. Reactions were initiated by the addition of enzyme. Initial rates during the period from 1 to 3 min. after the addition of enzyme were recorded on a Beckman Acta M-VI spectrophotometer. One control was run simultaneously with three test reactions, and all initial rates were adjusted to a common control rate. For further details of this procedure, see Randall et al., *J. Med. Chem.* 22, 6, 612 (1979).

The results obtained from this assay are illustrated below.

| Compound | IC$_{50}$ |
|---|---|
| 4-Hydroxy-5-phenyl-3(2H)—isothiazolone-1,1-dioxide | $2.1 \times 10^{-6}$ M |

The addition of halogen and $C_{1-6}$ alkyl substituents to the 5-phenyl moiety will serve to improve the inhibitory activity of the 4-hydroxy-5-substituted-3(2H)-isothiazolone-1,1-dioxide compounds since increased lipophilicity is desired in the aromatic substituent.

What is claimed is:

1. A compound of the formula:

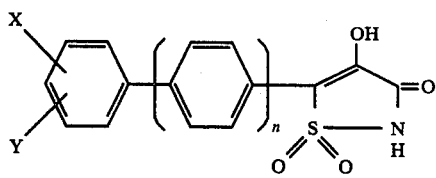

where
X and Y are independently selected from the group consisting of hydrogen, halogen, and $C_{1-6}$ alkyl; provided that positions 2 and 6 of the substituted phenyl moiety may not be substituted; and n is 0 or 1;
or a pharmaceutically acceptable salt thereof.

2. A compound according to claim 1 wherein X and Y are both hydrogen and the compound is 4-hydroxy-5-phenyl-3(2H)-isothiazolone-1,1-dioxide.

3. A compound according to claim 1 wherein the compound is 5-[4'-chloro-(1,1'-biphenyl)-4-yl]-4-hydroxy-3(2H)-isothiazolone-1,1-dioxide.

4. A compound according to claim 1 wherein the compound is 5-(3,4-dichlorophenyl)-4-hydroxy-3(2H)-isothiazolone-1, 1-dioxide.

5. A method of treating or preventing the formation of calcium oxalate urinary tract lithiasis, especially kidney or bladder stones, which comprises administering to a patient with, or prone to, such disease a therapeutically effective amount of a compound of the formula:

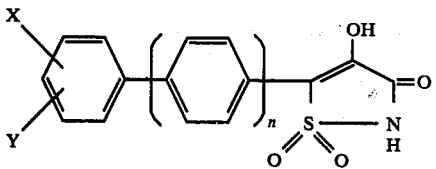

where
X and Y are independently selected from the group consisting of hydrogen, halogen, and $C_{1-6}$ alkyl; provided that positions 2 and 6 of the substituted phenyl moiety may not be substituted; and n is 0 or 1;
or a pharmaceutically acceptable salt thereof.

6. A method according to claim 5 wherein the thereapeutically effective amount is 50 mg. to 2000 mg. per day.

7. A method according to claim 5 wherein the compound administered is 4-hydroxy-5-phenyl-3(2H)-isothiazolone-1,1-dioxide.

8. A method according to claim 5 wherein the compound administered is 5-[4'-chloro-(1,1'-biphenyl)-4-yl]-4-hydroxy-3(2H)-isothiazolone-1,1-dioxide.

9. A method according to claim 5 wherein the compound administered is 5-(3,4-dichlorophenyl)-4-hydroxy-3(2H)-isothiazolone-1,1-dioxide.

10. A pharmaceutical composition for use in treating or preventing the formation of calcium oxalate urinary tract lithiasis, especially kidney or bladder stones, comprising a pharmaceutically acceptable carrier and a compound of the formula:

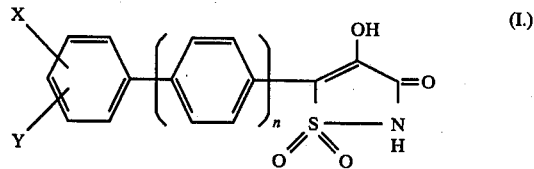

where
X and Y are independently selected from the group consisting of hydrogen, halogen, and $C_{1-6}$ alkyl; provided that positions 2 and 6 of the substituted phenyl moiety may not be substituted; and n is 0 or 1;
or a pharmaceutically acceptable salt thereof.

11. A composition according to claim 10 wherein the compound is 4-hydroxy-5-phenyl-3(2H)-isothiazolone-1,1-dioxide.

12. A composition according to claim 10 wherein the compound is 5-(3,4-dichlorophenyl)-4-hydroxy-3(2H)-isothiazolone-1,1-dioxide.

13. A composition according to claim 10 wherein the compound is 5-[4'-chloro-(1,1'-biphenyl)-4-yl]-4-hydroxy-3(2H)-isothiazolone-1,1-dioxide.

* * * * *